United States Patent [19]

De Domenico

[11] 4,353,247

[45] Oct. 12, 1982

[54] METHOD AND EQUIPMENT FOR THE IN SITU DETERMINATION OF GEOTECHNICAL PARAMETERS OF A SANDY SOIL

[76] Inventor: Rodolfo De Domenico, 40 Via Tommaso Gulli, Milan, Italy

[21] Appl. No.: 221,993

[22] Filed: Jan. 2, 1981

[51] Int. Cl.³ .............................................. G01N 3/08
[52] U.S. Cl. ....................................................... 73/84
[58] Field of Search ................... 73/84, 784, 821, 838, 73/839

[56] References Cited

U.S. PATENT DOCUMENTS 3,442,123  5/1969  Broise ..................................... 73/84
3,992,928  11/1976  Thoms ................................. 73/784

Primary Examiner—Herbert Goldstein
Attorney, Agent, or Firm—Fleit & Jacobson

[57] ABSTRACT

Method and equipment to determine, in situ, in a rigorous and repetitive way, the load bearing characteristics or geotechnical parameters of a sandy soil, according to the following phases: circumscribing, in situ, in the sandy soil, a sand sample, having a tubular, cylindrical shape, with a predetermined external diameter, a predetermined internal diameter, and predetermined length; applying to the sample, in correspondence to its internal, cylindrical surface, a radial pressure of predetermined value; and applying to the sample, in correspondence to its upper annular surface, an axial pressure, the value of which is made to increase to a value at which the sample ruptures. The geotechnical parameters are easily deduced from the value of axial pressure which causes the rupture, as well as from the values of the radial pressure and of the internal and external diameters of the sample itself.

3 Claims, 4 Drawing Figures

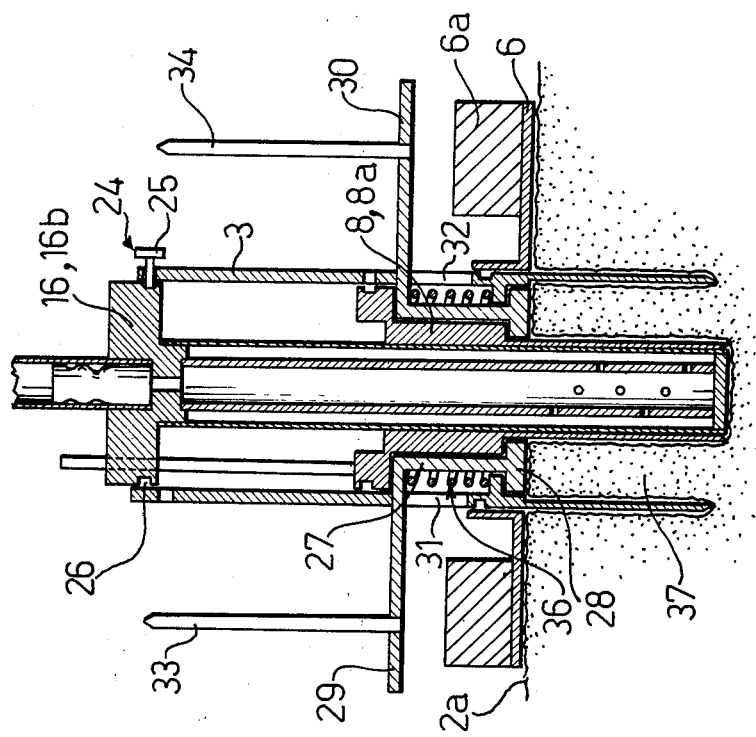
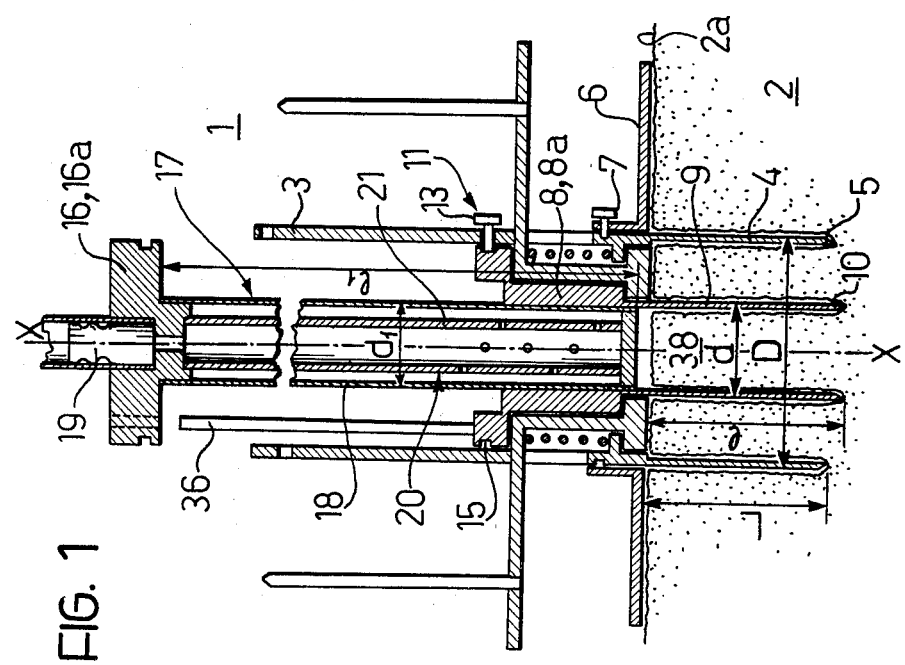

METHOD AND EQUIPMENT FOR THE IN SITU DETERMINATION OF GEOTECHNICAL PARAMETERS OF A SANDY SOIL

BACKGROUND OF THE INVENTION

Field of the Invention

The present invention relates to a method and apparatus for determining, in situ, geotechnical parameters of sandy soil. The term "geotechnical parameters" is intended to cover parameters of the soil relating to its ability to support loads.

As is known, when there is a need for constructing buildings or other works on sandy soil, one must plan and execute foundations corresponding to specific construction criteria, in relation to the load bearing characteristics or geotechnical parameters that the sandy soil itself presents.

Therefore, it is necessary to carry out accurate and reliable measurements on the sandy soil where one must build, to determine, in this way, the geotechnical parameters required to proceed with the planning of the foundations.

At present, such measurements are carried out by means of dynamic penetrometers, or static agents through multi-directional compression of the sandy soil from a simply driven point. Such a measuring method is empirical, and gives rise to measurements with a high repetition error.

SUMMARY OF THE INVENTION

The fundamental problem addressed by this invention is devising a method and related equipment to measure the load bearing characteristics or geotechnical parameters of a sandy soil, overcoming the previously discussed drawbacks encountered with known methods and equipment.

Such a problem is solved by a method which is characterized by its inclusion of the following phases:

circumscription, in situ, in the sandy soil, of a sand sample, having a tubular, cylindrical shape, with a predetermined external diameter, a predetermined internal diameter, and predetermined length; and applying to said sample, in correspondence to its internal cylindrical surface, a radial pressure of predetermined value;

applying to said sample, in correspondence to its upper annular surface, an axial pressure, the value of which is made to increase to a value at which the sample ruptures, the load bearing characteristics or geotechnical parameters being easily deduced from said value of axial pressure which causes the sample to rupture, as well as from said values of radial pressure and of the internal and external diameters of the sample.

This invention also consists of equipment to carry out the method described above, which is characterized by the fact that it includes:

a body having a rigid, tubular part with a predetermined diameter intended to be inserted to a predetermined length in the sandy soil, a first element having a rigid, tubular part of predetermined diameter, the first element being inside and coaxial with said body and being translatable with respect to and guided by said body, a second element having a cylindrical part with elastic walls of predetermined diameter, said second element being coaxial with and guided by the inside of said body for translation with respect to said body, said cylindrical part being inflatable, a third element having a rigid annular part extended between said rigid tubular parts to be supported on the surface of the sandy soil, said third element being inside and coaxial with said body and being guided by said body for translation with respect to said body.

Further characteristics and advantages of this invention will be made clear by the description of equipment according to the invention and of the method carried out with said equipment, made hereinafter with reference to the attached illustrations.

BRIEF DESCRIPTION OF THE DRAWINGS

In the detailed description of the preferred embodiments of the invention hereinafter presented, reference is made to the accompanying drawings, which are supplied for illustrative and not limitative purposes. In the drawings:

FIG. 1 is a schematic front sectional view of an apparatus according to the present invention in an initial operational position;

FIG. 2 is a view similar to FIG. 1 of the apparatus in a subsequent operational position;

DESCRIPTION OF THE PREFERRED EMBODIMENTS

Figure 4:
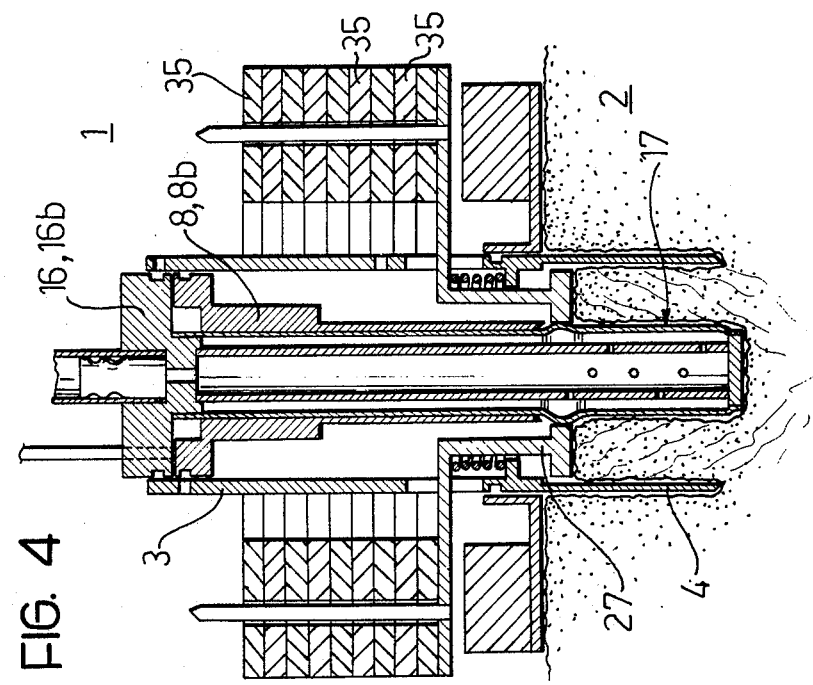
FIG. 4 is a view similar to FIG. 1 of the apparatus subsequent to rupture of the tested sample.

The following description will be directed, in particular, to elements forming part of, or cooperating more directly with, the present invention. Elements not specifically shown or described herein are understood to be selectable from those known in the art.

Referring now to the drawings, equipment or apparatus according to the invention, generally designated 1, is provided for measuring load bearing characteristics or geotechnical parameters of a sandy soil, identified with the reference numeral 2.

The equipment 1 comprises a body 3, preferably substantially tubular, with an axis x—x, which has a rigid, tubular, coaxial part 4 with a predetermined internal diameter D and predetermined length L. The part 4 is sharpened in correspondence with its edge 5, and is intended to be inserted in the sandy soil 2, with its axis "x—x" perpendicular to the surface 2a of the soil 2.

The body 3 is externally equipped with an annular platform 6 that is fixed to the body with screws 7. The platform 6 is intended to be supported on the surface 2a of the soil 2, when the part 4 is completely inserted in the soil 2. The platform 6, in turn, is equipped with ballasts, all shown by 6a. The equipment 1 also includes a first substantially tubular element 8. The element 8 is coaxial with and guided for translation with respect to the body, for instance, by the inside of the body 3. Said first element 8 has a rigid, coaxial, tubular part 9 with a predetermined external diameter d and predetermined length l.

The diameter d of said rigid, tubular part 9 has a value less than the diameter D of the rigid, tubular part 4, for example, a value equal to a third of the diameter D.

The length l of the tubular, rigid part 9 and the length L of the tubular, rigid part 4 are substantially equal and of a value equal at least to the diameter D of the tubular, rigid part 4.

The part 9 has sharpened edges 10 intended to be inserted in the sandy soil 2.

Figure 3:
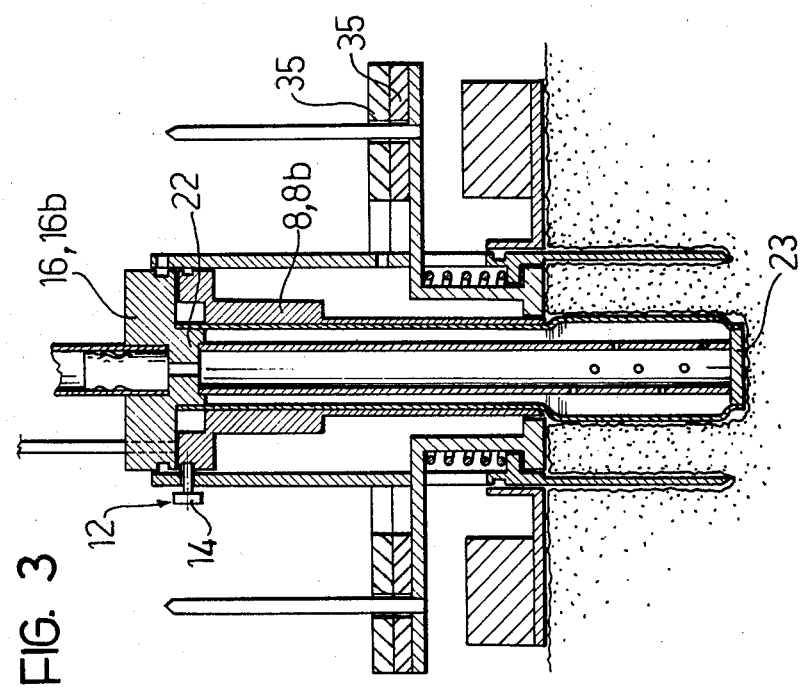
FIG. 3 is a view similar to FIG. 1 of the apparatus in an operational position subsequent to that illustrated in FIG. 2.

Clamping means, generally designated 11 and 12, unite the body 3 and the first element 8. The clamping means are alternatively operative, depending on whether said first element 8, sliding in the body 3, is located in an initial operative position, as illustrated 8a in FIG. 1, or in a second withdrawn position 8b, as illustrated in FIG. 3.

In the illustrated example, such means 11 and 12, respectively, include screws 13 and 14 selectively inserted through openings in the body 3, into engagement with a groove 15 formed in the first element 8.

Driving means, not illustrated, acting on a push rod 36, move said first element from the initial position 8a to the second position 8b, and vice versa.

The equipment 1 also includes a second, substantially tubular, element 16. The element 16 is coaxial with and guided for movement with respect to the body 3, for instance, by the insides of the wall of the body. Said second element 16 has a coaxial, cylindrical part, generally designated 17, having lateral, elastic walls 18 and an external diameter of predetermined value $d_1$ and predetermined length $l_1$. The diameter $d_1$ is chosen in such a way that the cylindrical, coaxial part 17 is inserted with limited play in the tubular, rigid part 9. The length $l_1$ is chosen in such a way as to be at least equal to said length l of the tubular, rigid part 9.

Conventional means, not illustrated in the drawing, feed, through a tube 19, the interior of said part 17 with a fluid under pressure, for example, compressed air, at a predetermined value of adjustable pressure. The compressed air determines the dilatation of said lateral elastic walls 18 of the cylindrical part 17.

The element 16 is equipped with a rigid structure 20 for the support of the cylindrical, coaxial part 17. The structure 20 includes a perforated pipe 21 with end plates 22 and 23 for clamping the elastic lateral walls 18.

The element 16 is movable, by the action of conventional means, not illustrated, from an initial withdrawn position 16a, as illustrated in FIG. 1, to a second operative position 16b in which the element is inserted in the soil, as illustrated in FIG. 2.

According to a variation in the implementation mode, the element 16, when it is not in its operative position 16b, can be completely removed from the body 3.

Clamping means, generally designated 24, releasably interconnect body 3 and and element 16 so that body 3 supports the element 16 in its position 16b. In the illustrated example, such means are formed by screws 25 engageable with a groove 26 formed in the element 16.

The equipment 1 also includes a third element, generally designated 27. The third element 27 is coaxial and guided for translation with respect to said body 3, for instance, by the inside of the wall of the body. The element 27 has a rigid, annular part 28 extended or located between the inside of the rigid, tubular part 4 and the outside of the rigid, tubular part 9. The annular part 28 is designed to rest on the surface 2a of the soil 2.

Said third element 27 has bracket parts 29 and 30 extended outwards through openings 31 and 32, respectively, made in the body 3. The brackets 29 and 30 are equipped with pointed wrist pins 33 and 34, extended upwards, according to the axial direction "x—x", intended to hold a plurality of calibrated weights, all shown by 35. Between the body 3 and the third element 27, elastic means 86 are interposed, dimensioned in such a way as to balance the weight of the third element 27, in the absence of calibrated weights 35.

With the equipment described above, it is possible to carry out the method to determine, in situ, the load bearing characteristics or geotechnical parameters of a sandy soil, according to this invention.

In an initial state, the equipment 1 has the first element 8 in its operative position 8a, and the second element 16 in its withdrawn position 16a. If necessary, the annular platform 6 is provided with some ballasts 6a, and the third element 27 is provided with some calibrated weights 35.

In this state, the equipment is set in operation, in situ, in the sandy soil, in such a way that the rigid, tubular parts 4 and 9 penetrate into the soil, thanks to their respective sharpened sides 5 and 10, and the annular platform 6 and the rigid, annular part 28 rest on the surface 2a of the soil 2.

In this way, in the sandy soil is circumscribed a sand sample 37 having a tubular, cylindrical shape, an external diameter equal to the diameter D of the rigid, tubular part 4, an internal diameter equal to the diameter d of the rigid, tubular part 9, an upper surface contacted by annular part 28, and length equal to the length L of the rigid, tubular part 4.

At this point (see FIG. 2), on the annular platform 6, ballasts 6a are placed, the weight of which is determined in such a way as to ensure stable operation of the equipment 1.

After having removed, manually or by some other conventional means, the sand 38 contained in the rigid, tubular part 9, the carriage 16 is brought from its withdrawn position 16a to its operative position 16b, in which the tubular, cylindrical part 17 occupies the rigid, tubular part 9. Compressed air at a predetermined pressure is then dispatched into the inside of the tubular, cylindrical part 17 to inflate the elastic walls 18.

Successively, the first element 8 is moved, by way of the rod 36, from its operative position 8a to its withdrawn position 8b in such a way that the rigid, tubular part 9 is extracted from the sandy soil 2. On the sand sample 37, in correspondence with its internal cylindrical surface, the elastic walls 18 of the cylindrical part 17, inflated as specified above, directly abut.

In this way, a radial pressure of predetermined value in relation to the pressure of the compressed air, is applied to said internal cylindrical surface of the sample 37. The value of the radial pressure is chosen in such a way as to ensure the firmness of the sample 37, even after extraction of the rigid, tubular part 9.

At this point (see FIG. 3), additional calibrated weights are gradually positioned on the brackets 29 and 30. In this way, said sand sample 37 is exposed, in correspondence to its upper annular surface, to an axial pressure from the annular, rigid part 28 of the third element 27. The value of the axial pressure increases gradually as calibrated weights 35 are added, one by one, until the pressure reaches a value at which the sample ruptures (see FIG. 4). Obviously, said axial pressure can be obtained by means of a completely conventional pneumatic piston cylinder unit, fed increasing pressure, as well as by means of calibrated weights 35.

On the basis of the dimensions of sample 37, and particularly of diameter D and diameter d, the value of the radial pressure, and the value of the axial rupture pressure, the load bearing characteristics or geotechnical parameters of the sandy soil 2 are easily deduced.

The main advantage of this method and of the equipment according to this invention is that they provide the opportunity for rigorous, repetitive measurements.

Actually, the measurement is taken by acting on a sample that is circumscribed and isolated from the surrounding soil, or, on a sample having finite dimensions and not on an indefinite continuum, as is sandy soil measured by traditional methods. Moreover, in the method according to the invention, test stress is applied according to perpendicular directions, coinciding with the principal directions of the sample, and not according to an indefinite plurality of directions, as under the methods of the technique noted.

Such perpendicular directions constitute the principal directions of the spatial tension system.

Hence, the mathematical model to elaborate analytically the measurement results designed to calculate all of the required load bearing characteristics or geotechnical parameters is much simpler than the mathematical model relative to the indefinite continuum.

A further advantage of the apparatus or equipment according to this invention is that it lends itself to determining the load bearing characteristics or geotechnical parameters of soils, either at or below the surface.

Actually, for use below the surface, the apparatus can easily be lowered into and maneuvered in a drilling hole of desired depth.

What is claimed is:

1. Method for the in situ determination of the load bearing characteristics of a sandy soil comprising the following phases:
    circumscribing, in situ, in the sandy soil, a sand sample having a tubular, cylindrical shape, with a predetermined external diameter, a predetermined internal diameter, and predetermined length;
    applying to said sample, in correspondence to its internal, cylindrical surface, a radial pressure of predetermined value;
    applying to said sample, in correspondence to its upper annular surface, an axial pressure, the value of which is made to increase to a value at which the sample ruptures;
    the load bearing characteristics being deduced from said value of axial pressure which causes the rupture, in combination with said values of the radial pressure and of the external and internal diameters of the sample.

2. Method for the in situ determination of the load bearing parameters of a sandy soil comprising the following phases:
    inserting in the sandy soil an initial, rigid, tubular part of predetermined diameter and predetermined length,
    inserting in the sandy soil a second, rigid, tubular part of predetermined diameter and predetermined length, in such a way as to circumscribe a cylindrical, tubular sand sample between the interior of the initial tubular part and the exterior of the second tubular part,
    removing sand contained in the interior of the second rigid, tubular part;
    inserting into the interior of said second rigid, tubular part an inflatable cylindrical part and inflating same to a predetermined value of pressure;
    extracting the second rigid, tubular part, so that said inflated cylindrical part applies to the internal, cylindrical surface of said sand sample a radial pressure of predetermined value;
    supporting, on the upper surface of the sand sample, a rigid, annular part; and
    adding weights having predetermined values to the annular part so as to apply to said sand sample a gradually increasing axial pressure until the rupture of said sample.

3. Apparatus for the in situ determination of the load bearing characteristics of a sandy soil comprising:
    a body having a rigid, tubular part of predetermined internal diameter insertable to a predetermined length in the sandy soil;
    a first element having a rigid, tubular part of predetermined external diameter coaxial with and guided for translation with respect to the inside of said body, said tubular part of said first element being insertable into the soil so that a cylindrical, tubular sample is circumscribed between the interior of the tubular part of said body and the exterior of said tubular part of said first element;
    a second element having a cylindrical part with inflatable elastic walls of predetermined diameter, said second element being coaxial with and guided for translation on the inside of said body, said cylindrical part with elastic walls being insertable into the interior of said tubular part of said first element;
    means for inflating said cylindrical part so that the inflated cylindrical part supports the interior of the tubular sample upon withdrawal of said first element;
    a third element having a rigid, annular part located between said rigid, tubular parts, said third element being coaxial with and mounted for translation with respect to said body, said rigid, annular part being intended to rest on the surface of the sample; and
    means for exerting a gradually increasing force on said annular part to thereby subject said sample to an increasing axial pressure.

* * * * *